United States Patent [19]
Berte' et al.

[11] Patent Number: 5,861,456
[45] Date of Patent: Jan. 19, 1999

[54] THICKENING COMPOSITIONS

[75] Inventors: Ferruccio Berte'; Giuseppe Raspanti, both of Bergamo, Italy

[73] Assignee: 3V Inc., Weehawken, N.J.

[21] Appl. No.: 552,866

[22] Filed: Nov. 3, 1995

[51] Int. Cl.$^6$ ........................................... C08K 5/05
[52] U.S. Cl. ..................... 524/556; 524/379; 524/385; 524/386; 524/387
[58] Field of Search ................................. 524/556, 379, 524/385, 386, 387

[56] References Cited

U.S. PATENT DOCUMENTS

| | | | |
|---|---|---|---|
| 2,798,053 | 7/1957 | Brown | 521/38 |
| 4,729,190 | 3/1988 | Lee | 47/57.6 |
| 4,748,220 | 5/1988 | Hartmann et al. | 526/89 |
| 4,923,940 | 5/1990 | Hsu | 526/208 |
| 5,149,463 | 9/1992 | Peterson | 252/301.21 |
| 5,346,986 | 9/1994 | Schneider et al. | 528/495 |
| 5,530,045 | 6/1996 | Brena et al. | 524/376 |

FOREIGN PATENT DOCUMENTS 0 712 897   5/1996   European Pat. Off. .

OTHER PUBLICATIONS

Journal of Polymer Science, Part A: Polymer Chemistry, vol. 26, No. 1, 1988, pp. 275–284, I. Iliopoulos et al, "Polymer Complexes Stabilized through Hydrogen Bonds. Influence of 'Structure Defects' etc.".

*Primary Examiner*—Marion McCamish
*Assistant Examiner*—John J. Guarriello
*Attorney, Agent, or Firm*—Griffin, Butler, Whisenhunt & Szipl, LLP

[57] ABSTRACT

The present invention relates to solid compositions of polymers or copolymers of unsaturated carboxylic acids partially or completely neutralized, a process for the preparation thereof and the use thereof as thickening agents.

12 Claims, No Drawings

THICKENING COMPOSITIONS

The present invention relates to solid compositions of polymers or copolymers of unsaturated carboxylic acids partially or completely neutralized, a process for the preparation thereof and the use thereof as thickening agents.

BACKGROUND OF THE INVENTION

The thickening agents based on polymers or copolymers of unsaturated carboxylic acids, mainly acrylic acid and the copolymers thereof have been known for a long time. They are used, generally in neutralized form, in a variety of industrial fields, for example to thicken cosmetic and pharmaceutical formulations, paints, inks, detergents, pastes for textile printing and the like.

The commercial products are in the form of powders or liquid formulations or pastes consisting of the thickening agent, generally in the neutralized form, dispersed in a water/oil phase of hydrocarbon type.

The powdered products in the acid form have the advantage of providing the thickening agent in the pure state, and are suitable when no undesired substances are to be introduced. However they are difficult to use since they are exceedingly pulverulent and moreover a time-consuming dispersion thereof in a solvent (generally water) and a subsequent neutralization are necessary.

Powdered products in the neutralized form are already commercially available, but they suffer from a problem of being highly pulverulent.

The liquid or paste formulations, on the contrary, are easy to use in the already neutralized form. The use thereof is widespread in the textile field for the preparation of printing pastes not only since they are easy to use, but also above all because they provide high quality prints as far as colour yield, uniformity and contour sharpness are concerned.

However, the use of liquid or paste formulations necessarily involves the introduction in the printing pastes of high amounts of volatile organic compounds (V.O.C.), which are released in the air during the production. Therefore, the presence of V.O.C. involves problems of safety and environmental pollution.

For these reasons, the market of the thickening agents for textile printing tends to employ easy-to-use formulations with a reduced V.O.C. content or even free from V.O.C..

Liquid formulations of thickening agents free from V.O.C. consisting of emulsion polymers (latexes) are also on the market. However, said products have a very low viscosimetric yield, and therefore they have to be used in large amounts when a high viscosity is required.

According to this trend, Canadian Patent 2,085,481 discloses the preparation of solid thickening agents already neutralized and free from volatile powders, and of course free from V.O.C.

Said products are acrylic acid polymers or copolymers, optionally cross-linked, obtained with techniques of inverse emulsion polymerization of acrylic acid salts and/or copolymers thereof. The preparation is carried out in the presence of polyalkylene glycols. The products are recovered by filtration after azeotropically removing the water from the system. The thickening agents obtained according to this process are substantially free from V.O.C. and dust-free. Their main use is the thickening of pastes for textile printing.

On the other hand, the compositions obtained according to this Patent involve some problems connected with the inverse emulsion preparation process. In particular, thickened gels of high transmittance, which is a paramount feature of many cosmetics in which the appearance is one of the more significant characteristics, cannot be prepared due to the presence of some synthesis additives which are water-insoluble, such as surfactants or the low HLB (hydrophilic-lipophilic balance) polymeric adjuvants necessary to prepare the inverse emulsion. Moreover, the resulting products are not very versatile, in fact they cannot be further formulated adding other ingredients conventionally used for textile printing pastes, to obtain ready-to-use formulations. As a matter of fact, the addition of other components during the polymerization step can negatively affect the process or the inverse emulsion destabilizing it, or make definitely more complex the process itself.

SUMMARY OF THE INVENTION

Surprisingly it has been found that ready-to-use solid compositions of polymers or copolymers of unsaturated carboxylic acids partially or completely neutralized can be prepared by neutralizing (also partially) the polycarboxylic polymers and/or copolymers thereof, obtained with specific polymerization techniques, and then mixing them with specific polyglycols by means of suitable processes. The presence of small amounts of inorganic or organic acid salts in these compositions improves the colour yield when the thickening compositions are used in the preparation of printing pastes. These compositions are dust-free, easily dispersible and free from V.O.C.. They give aqueous addensates with remarkable performances such as a high transmittance, which is useful in cosmetics, and the high colour yield and contour sharpness required for textile printing pastes.

Moreover, the process for the preparation of the solid compositions according to the present invention allows to easily introduce other ingredients in the basic formulation, as for example salts or surfactants, without significantly affecting the success of the process.

The thickening compositions in the solid form of the present invention consist of:

a) 70–98% w/w of polymers or copolymers and/or mixtures thereof, optionally cross-linked with a polyunsaturated compound, of an unsaturated carboxylic acid partially or completely neutralized with ammonia, amines or alkali metals;

b) 2–30% w/w of a polyglycol of formula:

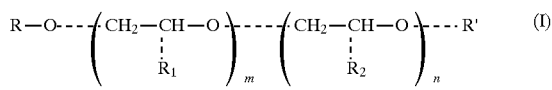

wherein R and R' can be the same or different and represent hydrogen, the —CH$_2$COOH group, straight or branched C$_1$–C$_8$ alkyl or optionally substituted phenyl, R$_1$ and R$_2$ are the same or different and are hydrogen, the methyl or ethyl group; and the expression:

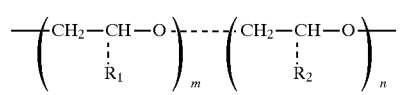

means that the units:

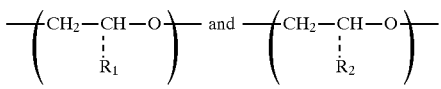

can be present in any order, random or in blocks; n and m can be the same or different and can have values ranging from 0 to 5,000 with the proviso that the sum thereof is at least 2;

c) 0–28% w/w of a salt of an acid with ammonia, amines and/or alkali metals;

characterized in that the polymers of component a) are obtained by means of precipitation polymerization techniques.

DESCRIPTION OF PREFERRED EMBODIMENTS

The polymer thickening agents according to the present invention are the polymers or the copolymers, preferably cross-linked, of unsaturated carboxylic acids, conventionally used in this technical field, such as: acrylic, methacrylic, crotonic, sorbic, itaconic, maleic, fumaric and 3-acryloxypropionic acid. In the case of copolymers, these contain at least 70% w/w of the above cited unsaturated acids. Possible comonomers are, for example, the esters of the above mentioned unsaturated carboxylic acids with alcohols containing 1 to 30 carbon atoms or with alcohols or phenols polyethoxylated and/or polypropoxylated, hydroxyalkylacrylates or methacrylates, alkoxyalkylacrylates or methacrylates, acrylonitrile, methacrylonitrile, acrylamide or methacrylamide and N-substituted derivatives thereof, vinyl alcohol esters, vinyl ethers, ethylene, propylene, styrene and butadiene monomers.

These carboxylic polymers are preferably cross-linked with polyunsaturated compounds such as: divinyl benzene, allyl acrylates and methacrylates, glycol diacrylates and dimethacrylates, 1,7-octadiene, butadiene, triallylcyanurate or isocyanurate, allylacrylamide or allylmethacrylamide, methylenebisacrylamide and particularly polyallyl ethers of polyols such as polyallyl sucrose, polyallyl pentaerythritol and divinylglycol.

According to the present invention, the carboxylic polymers are obtained with techniques of precipitation or dispersion polymerization from solvents such as: benzene, methylene chloride, aliphatic and/or aromatic hydrocarbons, halogenated hydrocarbons, esters, ethers, ketones and mixtures thereof or carbonic anhydride.

The processes for the preparation of these polymers are well known and described for example in U.S. Pat. Nos. 2,798,053, 2,980,655, 3,940,351, 3,915,921, 4,923,940 and in EP-A- 239,035.

The salts of these polymers or the mixtures thereof are the component a) of the compositions according to the present invention and are preferably obtained by total or partial neutralization of the acid form at the end of the polymerization in the same synthesis solvent or after recovery of the same form and subsequent neutralization in the presence or not of another solvent. For example, in the case an ammonium salt is desired, neutralization can be carried out very easily either by contacting the powder of the polyacid with gaseous ammonia or by blowing ammonia into the dispersion of the acid polymer in a solvent such as cyclohexane or methylene chloride. In order to prepare a sodium or potassium salt, for example, the polycarboxylic acid can be suspended in alcohols such as methanol, ethanol and/or isopropanol and then neutralized with sodium and/or potassium hydroxides, oxides or carbonates.

In order to isolate the neutralized form of the polycarboxylic acid, it is sufficient to remove the solvent, for example by distillation.

The polyglycols of formula (I) according to the invention are polymers or copolymers obtained from ethylene oxide and/or propylene oxide and/or butylene oxide, or they are polycondensates of the oxides cited above with aliphatic alcohols or optionally substituted phenols, in which the value of the sum m+n is higher than 2 and preferably it ranges from 3 to 250.

Said compounds are commercially available (see International Cosmetic Ingredient Dictionary—5th Ed. 1993).

The compounds constituting the component c) of the compositions of the present invention are the salts of organic and inorganic acids, preferably those of strong acids with ammonia, amines and/or alkali metals and the mixtures thereof such as ammonium and/or sodium and/or potassium chlorides, sulfates, carbonates, phosphates, citrates.

The compositions according to the present invention can be prepared directly mixing homogeneously the components a), b) and optionally c). Preferably, they are prepared mixing the components in the presence of a solvent system which can be the same as or different from that used for the synthesis of the polycarboxylic acid and then removing the solvent itself, for example by distillation. Due to its nature, the process according to the present invention allows also to introduce other additives, for example surfactants, without any negative influence on the process. Moreover, the order in which the components a), b) and c) are added can be varied suitably since the quality of the compositions obtainable is not significantly affected.

The solvents used in the process according to the present invention are aliphatic, aromatic and/or halogenated hydrocarbons, esters, ketones, alcohols, ethers and the mixtures thereof. Hexane, cyclohexane, octane, methylene chloride, ethyl acetate, ethyl formate, methylal, dimethyl carbonate, isopropanol, ethanol, methanol and mixtures thereof, can preferably be used.

The solid compositions according to the present invention are characterized by the absence of V.O.C. and are easy-to-use. In particular, they are non-pulverulent, do not soil surfaces, have good flowability and are easy to disperse in the aqueous systems, quickly and completely exerting their thickening power without requiring the use of particularly fast or specific stirrers.

The aqueous addensates obtained by means of the solid compositions according to the present invention are homogeneous and have the rheological properties characteristic of the neutralized polycarboxylic acids which the compositions are prepared from.

In particular, addensates with high transmittance can be obtained only containing already used, authorized substances for cosmetics. These characteristics are absolutely necessary in many cosmetic formulations, such as in gel products or in creams in which a particularly clear appearance is required.

The aqueous addensates obtained by means of the solid compositions according to the present invention can also be used in the formulation of pastes for textile printing. They turn out to be nearly free from V.O.C. and allow to obtain high quality prints as far as the colour yield and contour sharpness are concerned.

The use of the solid thickening compositions according to the present invention in the preparation of formulated addensates involves no difficulty and can be carried out by means of conventional techniques known to those skilled in the art.

The compositions according to the present invention are used in amounts and with procedures from time to time suitable to the final formulation desired. The amounts and the procedures are chosen by those skilled in the art and further details are not required in this disclosure. For example, the compositions according to the present invention can be used in amounts ranging from 0.05 to 10%, preferably from 0.1 to 5.0% by weight with respect to the total weight of the composition.

The following examples illustrate the present invention further.

EXAMPLE 1

98.65 g of acrylic acid, 0.85 g of pentaerythritol polyallyl ether and 0.50 g of di-lauroyl-peroxide in 735 g of cyclohexane are stirred at 70° C. for 10 hours. The resulting slurry, containing 100 g of cross-linked polyacrylic acid is cooled and treated with 16.23 g of gaseous ammonia. Then 22.5 g of polyethylene glycol 400 are added.

From the final slurry, removing the solvent, 122.5 g of product are obtained in the form of an agglomerated powder, which is flowable, non-pulverulent, easy to use, and when dispersed by 0.5% w/w in demineralized water produces in a few minutes a gel with viscosity of 21,000 mpa.s (Brookfield RVT-20° C.—20 rpm).

COMPARATIVE EXAMPLE 1

The process of Example 1 is repeated without adding polyethylene glycol 400. A very fine powder is obtained which is difficult to use since it is less flowable and a lot more pulverulent.

EXAMPLE 2

98.18 g of acrylic acid, 1.32 g of pentaerythritol polyallyl ether and 0.50 g of di-(tert-butylcyclohexyl)peroxydicarbonate in 1,000 g of methylene chloride are stirred under reflux for 10 hours. The resulting slurry, containing 100 g of cross-linked polyacrylic acid, is cooled and treated with 16.23 g of gaseous ammonia. Then 16.6 g of diammonium phosphate (<100 micron) with stirring and then 18.0 g of polyethylene glycol 400 are added.

From the final slurry, removing the solvent, 150.8 g of a product are obtained in the form of an agglomerated powder which is flowable, non-pulverulent, easy to use and when dispersed by 0.5% w/w in demineralized water produces in a few minutes a gel with viscosity of 6,000 mPa.s (Brookfield RVT- 20° C.—20 rpm).

EXAMPLE 3

100 g of Stabilen 30® (acrylic acid cross-linked copolymer manufactured by 3VSigma-Italy) are suspended in 1,000 g of methylene chloride. The resulting slurry is treated with 14.6 g of gaseous ammonia. Then 18.5 g of polyethylene glycol 400 and 8.5 g of ammonium sulfate (<100 micron) are added. By removing the solvent, 141.6 g of a product in the form of an agglomerated powder are obtained which is easy to use and quickly dispersible.

EXAMPLE 4

100 g of Carbopol 980® (cross-linked polyacrylic acid manufactured by B.F. Goodrich—USA) are placed into a suitable mixer, for example of the type EL 1-E. Schweizer Co. Apparatebau, and treated in the dry state with 18 g of gaseous ammonia. The resulting ammonium salt is added with 16 g of diammonium citrate (<100 micron) and 18 g of polyethylene glycol 400. 152 g of a product are obtained, in the form of an agglomerated powder which is easy to use and quickly dispersible in water.

EXAMPLE 5

60 g of sodium hydroxide are dissolved in 650 ml of methanol. The resulting solution is added with 144 g of Acrisint 400® (cross-linked polyacrylic acid by 3V Sigma-Italy) at a temperature from 10° to 60° C., with stirring. Subsequently, 18 g of polyethylene glycol 400 are added, stirring again for 30 minutes, then the mixture is evaporated to dryness under vacuum until constant weight.

195 g of a product are obtained, in the form of a flowable powder which is non-pulverulent and easy to use.

EXAMPLES 6–10

125 g of Acrisint 400® are treated in the dry state, with stirring, with 22 g of gaseous ammonia. The resulting ammonium salt is subdivided into five portions. Each portion is dispersed in a solution consisting of 60 g of a polyglycol in 200 g of methylene chloride. By removing the solvent, in all the cases a flowable product is obtained, which is non-pulverulent and easily dispersible in water. The polyglycols used in each example are reported in Table 1.

TABLE 1

| Example | Polyglycol |
| --- | --- |
| 6 | polyethylene glycol 35,000 |
| 7 | polyethylene glycol 5,000 monomethyl ether |
| 8 | polyethylene glycol 600 diacid |
| 9 | pluronic L43$^R$ copolymer ethylene oxide propylene oxide — BASF) |
| 10 | polyethylene glycol 100,000 |

EXAMPLE 11

Three printing pastes are prepared for printing on a 55 threads/cm frame for cotton fabric and 71 threads/cm frame, for polyester/cotton fabric 65:35, using the following ingredients:

| | |
| --- | --- |
| Hard water (25° F.) | to 1,000 g |
| Defoprint A$^R$ | 2 g |
| Thickening agent | 12 g |
| Ammonia 25% | 4 g |
| Legoprint EPC$^R$ | 120 g |
| Fixol ST$^R$ | 10 g |
| Blue pigment Helizarin RT | 30 g |

The first paste is prepared with a thickening agent obtained according to example 1 of Canadian Patent 2,085, 481 in which the water-in-oil polymer n. 1 is neutralized to pH 7 with aqueous ammonia (PASTE A).

The second paste is prepared with the thickening agent of example 1 of the present invention (PASTE B).

The third paste is prepared with the thickening agent of example 2 of the present invention (PASTE C).

The final pH of the pastes is 8.5–9.0 and the viscosities thereof are about 17,000–18,000 mPa.s (Brookfield RVT—20° C.—20 r/min).

The prints are carried out on a printing machine ZIMMER MINI MDF R 376. The printed fabrics are finally treated in a drying chamber for 3 minutes at 160° C. and visually evaluated by direct comparison on the basis of colour yield, penetration, uniformity and contour sharpness. Each parameter is scored from 0 to 4 wherein:

0=insufficient (very penetrated prints)
1=sufficient
2=quite sufficient
3=good
4=very good (very superficial prints)

The results obtained are shown in Table 2.

TABLE 2

|  | PASTE A | PASTE B | PASTE C |
|---|---|---|---|
| COLOUR YIELD | 2 | 3 | 4 |
| PENETRATION | 2 | 3 | 4 |
| UNIFORMITY | 2 | 2 | 2 |
| CONTOUR SHARPNESS | 2 | 2 | 2 |

EXAMPLE 12

2.00 g of thickening composition of example 5 are dispersed in 298 g of demineralized water to obtain in a few minutes a clear gel of viscosity 45,000 mPa.s (RVT—20° C.—20 rpm) and 94% transmittance (10 mm thickness—425 nm wavelength—double-beam spectrophotometer).

A similar preparation carried out using a thickening composition obtained operating according to the procedure described in example 6 of Canadian Patent 2,085,481 gives a viscous but turbid gel in a longer time.

We claim:

1. A thickening composition in powder form, comprising:
   a) 70–98% w/w of polymers or copolymers and/or mixtures thereof, optionally cross-linked with a polyunsaturated compound, of an unsaturated carboxylic acid salt with ammonia, an amine, or an alkali metal;
   b) 2–30% w/w of a polyglycol of formula (I):

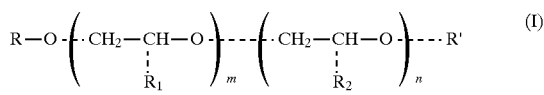

wherein R and R' can be the same or different and represent hydrogen, the —CH$_2$COOH group, straight or branched C$_1$-C$_8$ alkyl, or optionally substituted phenyl; R$_1$ and R$_2$ are the same or different and are hydrogen, methyl, or ethyl; and the expression:

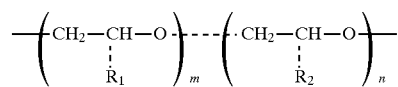

means that the units:

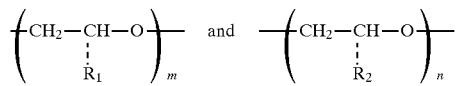

can be present in any order, random or in blocks; n and m can be the same or different and can have values ranging from 0 to 5,000 with the proviso that the sum thereof is at least 2;

c) 0–28% w/w of a salt of an acid with ammonia, amines, and/or alkali metals;

wherein the polymers or copolymers of component a) are obtained by means of precipitation polymerization.

2. The composition of claim 1, wherein the unsaturated carboxylic acid of component a) is selected from the group consisting of acrylic acid, methacrylic acid, crotonic acid, sorbic acid, itaconic acid, maleic acid, fumaric acid, and 3-acryloxypropionic acid.

3. The composition of claim 2, wherein, in component a), the unsaturated carboxylic acid is at least 70% w/w acrylic and/or methacrylic acid.

4. The composition of claim 1, wherein the monomers reacted with said unsaturated carboxylic acid to form said copolymers are esters of unsaturated carboxylic acids selected from the group consisting of acrylic acid, methacrylic acid, crotonic acid, sorbic acid, itaconic acid, maleic acid, fumaric acid, and 3-acryloxypropionic acid with alcohols selected from the group consisting of alcohols containing 1 to 30 carbon atoms and polyethoxylated and/or polypropoxylated aliphatic alcohols or phenols or are hydroxyalkylacrylates or methacrylates, alkoxyalkylacrylates or methacrylates, acrylonitrile, methacrylonitrile, acrylamide, methacrylamide, vinyl alcohol esters, vinyl ethers, ethylene, propylene, styrene, or butadiene.

5. The composition of claim 1, wherein the polymers or copolymers component a) are cross-linked with a compound selected from the group consisting of divinyl benzene, allyl acrylates and methacrylates, glycol diacrylates and dimethacrylates, 1,7-octadiene, butadiene, triallyl cyanurate or isocyanurate, allylacrylamide or allylmethacrylamide, methylenebisacrylamide, and polyol polyallyl ethers.

6. The composition of claim 1, wherein component b) consists of a polyglycol of formula (I) in which the sum n+m ranges from 3 to 250.

7. The composition of claim 1, wherein component c) consists of a salt of an acid selected from the group consisting of hydrochloric acid, nitric acid, sulfuric acid, phosphoric acid, acetic acid, citric acid, tartaric acid, methanesulfonic acid, toluenesulfonic acid, and xylenesulfonic acid with a base selected from the group consisting of ammonium hydroxide, sodium hydroxide, and potassium hydroxide, or a mixed salt or a mixture of salts.

8. The composition of claim 1, wherein the polymers and copolymers of component a) are in the form of a salt obtained by partial or total neutralization of the polymer or copolymer at the end of the polymerization in a synthesis solvent or after recovery of the polymer or copolymer and subsequent neutralization in the absence or presence of a solvent.

9. A process for the preparation of the composition of claim 1, which comprises admixing components a), b), and optionally c).

10. A cosmetic product comprising 0.1 to 5% by weight with respect to the total weight of the cosmetic product of a composition of claim 1 as thickening agent.

11. A composition according to claim 1, containing components for formulation into cosmetic, pharmaceutical, paint, ink, detergent, and textile printing compositions.

12. A composition according to claim 1, containing surfactants.

* * * * *